United States Patent [19]
Zetter

[11] Patent Number: 6,078,389
[45] Date of Patent: Jun. 20, 2000

[54] MULTIVARIATE SPECTROSCOPY WITH OPTICAL COMPUTATION

[76] Inventor: Mark S. Zetter, 757 Marina View Dr., El Dorado Hills, Calif. 95762

[21] Appl. No.: 09/376,542

[22] Filed: Aug. 18, 1999

[51] Int. Cl.⁷ ....................................................... G01J 3/00
[52] U.S. Cl. ........................................... 356/300; 356/310
[58] Field of Search ..................................... 356/300, 326, 356/310; 250/339.01, 339.02, 339.07, 339.12

[56] References Cited

PUBLICATIONS

Myrick et. al., *Analytical Chemistry*, 1998, 70, 73–82.

*Primary Examiner*—F. L. Evans
*Attorney, Agent, or Firm*—Eugene I. Snyder

[57] ABSTRACT

A method is presented to perform accurate property measurements using spectroscopic measurements at multiple wavelengths using nondispersed radiation with one, or sometimes two, detectors sensing all the requisite wavelengths simultaneously and calculating the value of the property by optical means. The heart of our invention is the utilization of an optical device opaque everywhere but at the finite and limited number of wavelengths where the transmittance measurements are being made, and whose transmittance at the measuring wavelengths is proportional to the coefficient for that wavelength in a predictive equation for the property value. The process which is our invention passes nondispersed light through a sample, with the transmitted light being led onto an optical device passing only the measuring wavelengths onto a detector. The optical device transmittances at the measuring wavelengths are proportional to the coefficients for those wavelengths, so that the total light passing through the optical device is actually proportional to the value of the property being measured. Our method leads to substantial reduction in instrument costs through simplified design and a reduction in components, with concomitant increased ease of use, and the elimination of the need for ancillary computational means.

4 Claims, 1 Drawing Sheet

MULTIVARIATE SPECTROSCOPY WITH OPTICAL COMPUTATION

BACKGROUND OF THE INVENTION

Spectroscopy has been a reliable, omnipresent, powerful tool for both qualitative and quantitative analysis. In its qualitative aspects a variety of spectroscopic techniques have been employed, alone or in combination, to identify materials or their components. In its quantitative aspects spectroscopic methods have been most commonly employed to determine such primary properties as concentration, or the amount of one or more components in any material. More recently spectroscopic measurements have been performed at multiple wavelengths with attendant multivariate analysis of transmittances at the measured wavelengths to calculate derived properties such as octane number or a physical property such as polymer melt index. This technique is very general, and merely posits a relationship between some totality of wavelength-transmittance measurements and the derived property, e.g., octane number, a relationship which is determined via appropriate analysis (partial least squares, principal component regression, multiple linear regression, etc.) of substrates with known values of octane number to afford a predictive equation for the domain established by the substrate sample class. The equation has the form, $$P = K + \sum_{j=1}^{n} b_j T_j \quad (1)$$

where P is the property to be measured, $T_j$ are the transmittances of light at wavelength j, n is the number of wavelengths at which measurements are made, and $b_j$ are the coefficients determined from multivariate analysis. Although this technique of multiple wavelength analysis is most often applied to what we refer to above as derived properties, it also can be used advantageously for measuring the concentration of a component, particularly where 1 or more interfering substances are present. By "interfering substances" we mean substances which have significant absorbtion at those wavelengths commonly used to measure the concentrate of the analyte in question.

To date the foregoing technique using measurements at multiple wavelengths in conjunction with a predictive equation employ computational methods subsequent to, and independent of, the spectroscopic measurements themselves. In addition, measurements at multiple wavelengths generally employ means to separate a broadband energy source into its component wavelengths, as by use of a diffraction grating or prism mounted on a rotatable platform which disperses the electromagnetic radiation into discrete wavelengths, with a different wavelength falling on the sample as the rotation angle changes. This requires cumbersome and delicate mechanisms which substantially increase instrument cost. An alternative is to have nondispersed light pass through the sample, then disperse the transmitted light into discrete wavelengths, each of which falls on a separate diode in a diode array. This approach, however elegant, also results in increased instrumental complexity and increased instrument cost.

The broad purpose of our invention is to perform accurate property measurements using spectroscopic measurements at multiple wavelengths, but using 1) nondispersed radiation with but a single detector—or in some cases two detectors—sensing all the requisite wavelengths simultaneously, and 2) optical calculation of the property but without needing the usual computational accoutrements. This leads to substantial reduction in instrument costs through simplified design and a reduction in components, with concomitant increased ease of use, and the elimination of the need for ancillary computational means.

Our invention is applicable to spectroscopy generally, whether based on the intensity of electromagnetic radiation transmitted, reflected, emitted, or scattered. Because we employ optical methods our invention is directed to spectroscopy where the electromagnetic radiation has a wavelength in the range from about 150 nm to about 15,000 nm. Aside from this restriction it will be seen that our invention is quite broad and quite general in its application to spectroscopy.

It needs to be mentioned that Myrick et al., *Anal. Chem.*, 1998, 70, 73–82 have recognized that it should be possible to process multiwavelength spectra by passing the multiwavelength light, without dispersion, through a filtering mask with wavelength-dependent transmittance factors onto a common detector. Myrick's implementation, however, is substantially different from ours. In particular, the authors' mask represents a regression vector as a continuous function over the entire wavelength range, i.e., it is a homogeneous filter; the authors note the difficulty of fabricating such a mask or filter. In our invention the mask represents a discontinuous function, with the filter being everywhere opaque except at a relatively small number of wavelengths where measurements are made. As we note within, such filters are easily fabricated in several ways; there is no problem with filter fabrication as there is with the implementation of Myrick et al. Our filter can be viewed as a massively parallel filter, or mosaic filter, in contrast to the authors' implementation.

SUMMARY OF THE INVENTION

The purpose of our invention is to determine the value of a property of a substance using spectroscopic measurements at multiple wavelengths employing nondispersed radiation and optical computation of the property in question. In an embodiment, a finite and limited number of wavelengths of electromagnetic radiation is passed through a sample, conducted thereafter to an optical device everywhere opaque except at the measuring wavelengths and where the transmission of light at each measured wavelength is proportional to the coefficient for that wavelength in a predictive equation of the form, $$P = K + \sum_{j=1}^{n} b_j I_j$$

DESCRIPTION OF THE INVENTION

Figure 1:
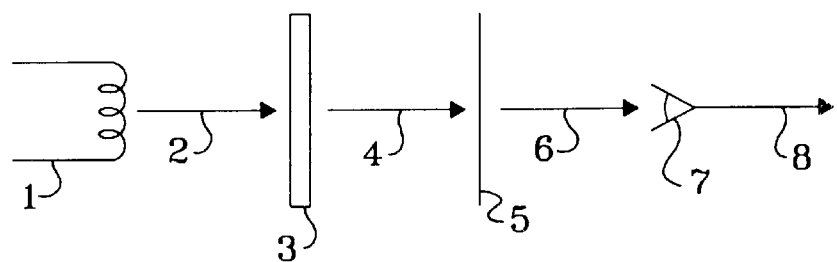
FIG. 1 is a diagrammatic representation of spectroscopic measurements using the optical device of our invention and a single detector.

The heart of our invention utilizes an optical device opaque everywhere but at the wavelengths where radiation intensity measurements are being made, and whose intensity of radiation passing through the device at the measuring wavelengths is proportional to the coefficient for that wavelength in the predictive equation. The process which is our invention passes nondispersed light, which encompasses the measuring wavelengths, through a sample. Transmitted light is led onto an optical device which passes only the measuring wavelengths onto a detector. The optical device transmittances at the measuring wavelengths are proportional to the coefficients for those wavelengths, so that the total light passing through the optical device is actually proportional to the value of the property being measured. Assuming the light source radiation and the detector response is equal for all measuring wavelengths, or properly compensated for, the detector response is then also positively or negatively proportional to the property being measured, and by incorporation of suitable electronic circuitry the value of the property can be "read" directly from the output. The foregoing can be readily demonstrated and understood by the following analysis.

We start with the Beer-Lambert law, fundamental to all spectroscopy, which states that the transmittance of a sample is exponentially related to the concentration of the chromophore in that sample, i.e., $$T = I/I_o = 10^{-ecl}$$

where Io is the null intensity of light, I is the intensity of light passing through the sample, e is the extinction coefficient of the chromophore at the measuring wavelength, c is the concentration of the chromophore in the sample, and l is the sample (and null!) path length. Note that 100×T=percent light transmitted through the sample. It then follows that:

$$log(I/I_o) = -ecl$$

$$c = A log(I_o/I)$$

The concentration c is merely representative of a property whose value depends upon the number of molecules having the relevant chromophore; it is a measure of the number of relevant molecules. The Beer-Lambert law could equally well be written as:

$$P = A log(I_o/I) = -A log(I/I_o) = -A log T \quad (2)$$

where P is any property and T is the transmittance. It should be clear that the value of A will depend upon which property P is being measured.

If one performs a Taylor expansion on (2), then $$-A log T = -A[(T-1) + 1/2(T-1)^2 + \ldots + 1/n(T-1)^n]$$

For values of T close to 1—which means at high transmittance—logT can be well approximated by the first term of the series expansion, thus, $$P = -A log T = A(1-T) = A - AT = A - A(I/I_0)$$

That is, the value of the property P increases linearly with a decrease in intensity of light passing through the sample. What is important to recognize is that the value of the measured property varies linearly with intensity of light passing through the sample. Given the approximations, and putting aside for the moment the sign of the coefficient, one can express P more generally as $$P = A + BI$$

Since this relationship is true for every value of wavelength used, one then can write $$P_j A_j + B_j I_j$$

for every wavelength j, with P being the same for every wavelength. It then follows that:

$$P = 1/n \sum A_j + B_j I_j = K + \sum_{j=1}^{n} b_j I_j \quad (3)$$

Thus, the value of the property can be determined by summing the product of a coefficient, $b_j$, unique for every wavelength j, by the intensity of light passing through the sample at that wavelength, $I_j$. This is exactly the basis of applying multivariate analysis to a sample using multiple wavelength measurements, and it will be recognized that the foregoing equation is the predictive equation given earlier. In our invention we use at least 2 different wavelengths, but generally not more than 100, and usually measurements are made at not more than 50 different wavelengths. That is, $2 \leq n \leq 100$, and more usually $2 \leq n < \leq 50$.

Measurements at multiple wavelengths are advantageous in providing a result more accurate than measurement at a single wavelength, in providing a result which is less instrument-dependent, and in providing a result less susceptible to interfering substances. Typically, a set of samples with known values of the property of interest are used to establish a sample space and serve to determine the value of the coefficients at the measuring wavelengths. Suitable calibration methods are well known in the art and will not be further elaborated except to note that they are performed using classical spectrophotometers and well-established methodology. Nonetheless, the disadvantages of multiple wavelength measurements as performed by prior art methods are the need for relatively complex, expensive instrumentation to perform measurements at many discrete wavelengths (i.e., classical spectrophotometers), and the need for extensive post-measurement calculation. Our invention circumvents both of these disadvantages.

As previously stated, the prior art utilizes a typical spectrometer which measures the transmission as a function of wavelength by measuring one wavelength at a time, either by using a device to vary the wavelength of light hitting a detector, e.g., a grating or acousto-optic crystal, or by irradiating an array of detectors, such as a diode array, with a range of wavelengths simultaneously where the light has been previously dispersed by, e.g., a grating. A computer program or computational electronic circuit will then use the coefficients in equation (3)—or its absorbance equivalent—together with the spectrum to calculate the final result, P. Our invention provides a simpler method, far less expensive and cumbersome than the prior art, of measuring P at multiple wavelengths. Central to our invention is the use of only a single detector—or in some cases two detectors—receiving light simultaneously from all wavelengths required for measurement, where the a mount of light at each measuring wavelength is scaled in proportion to the coefficients in the predictive equation (3).

Some examples will help to clarify our invention. Consider the case where measurements are taken at four wavelengths, 1200, 1625, 1700, and 1920 nm., and that calibration gave values of b as 1,2,0.5, and 4, resp. The relevant equation would be:

$$P - K = 1.0 I_{1200} + 2.0 I_{1625} + 0.5 I_{1700} + 4 I_{1920} \quad (4)$$

Assume an optical device constructed with the optical characteristics of zero transmission at all wavelengths except 1200, 1625, 1700, and 1920 nm, with the ratio of transmission at the foregoing wavelengths being 1:2:0.5:4, i.e., the ratio of transmission at 1200, 1625, 1700 and 1920 nm is exactly the same as the ratio of coefficients in equation (4) for these wavelengths. Let us now apply a normalization factor, F, to (4) such that F multiplied by the largest coefficient, b, is equal to 1. We then have $$F(P-K) = Fb_{1200}I_{1200} + Fb_{1625}I + Fb_{1700}I_{1700} + Fb_{1920}I_{1920} \quad (5)$$

In terms of the optical device the window with the largest transmitting characteristics would transmit 100% of the light. Equation (4) then becomes (in our example)

$$0.25(P-K) = 0.25I_{1200} + 0.5I_{1625} + 0.125I_{1700} + I_{1920} \quad (6)$$

Now consider this optical device in the simple optical scheme of FIG. 1. Incident light 2 from the light source 1 is conducted to the sample, 3, and light transmitted through the sample, 4, is conducted to the optical device 5. Light transmitted through the optical device, 6, has its intensity at each measured wavelength scaled according to the coefficient in the predictive equation. The transmitted and scaled light is then conducted onto a single detector, 7, with its electrical output 8 processed by suitable electronic means. In effect this takes the transmission values at the four wavelengths and multiplies the sample transmission at each wavelength by the relevant coefficient. The light falling on the detector is then proportional to the left hand side of (6). In other words, an optical computation has been performed at all wavelengths truly simultaneously and without dispersion of the light with attendant losses of that process. This simultaneous optical measurement at multiple wavelengths cannot be performed even with a diode array approach, since the scanning of the array takes time albeit milliseconds or less. It is important to recognize that such measurement has occurred a) without dispersion of light, b) using a single detector, and c) without independent computation.

Figure 2:
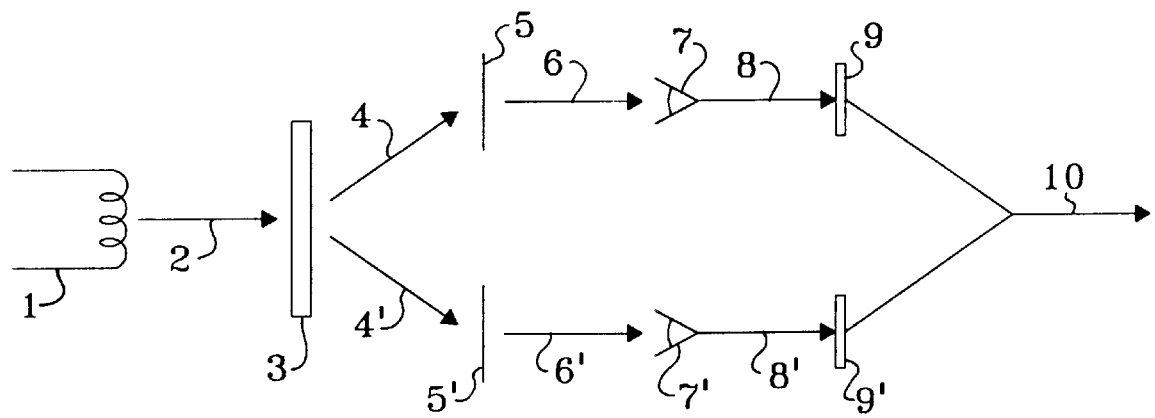
FIG. 2 is a diagrammatic representation of spectroscopic measurements using two optical devices of our invention and two detectors where the measured property is proportional to the difference in detector signals.

There is another practical aspect to our invention It may be that some of the coefficients in (6) are negative and having negative optical transmission is not a practical reality. This situation may be solved by breaking the equation and its corresponding optical device into two parts, one for positive and one for negative coefficients. Assuming in (6) that coefficients are negative at 1625 and 1920 nm, the equation can be restated as $$0.25(P-K) = 0.25I_{1200} - 0.5I_{1625} + 0.125I_{1700} - I_{1920} \quad (7)$$

$$0.25(P-K) = 0.25I_{1200} + 0.125I_{1700} - (0.5I_{1625} + I_{1920}) \quad (8)$$

$$0.25(P-K) = X - Y,$$

where $X = 0.25I_{1200} + 0.125I_{1700}$, and $Y = 0.5I_{1625} + I_{1920}$. This presents a situation where one optical device could represent A (contributors with positive coefficients) and another could represent B (contributors with negative coefficients), with both inserted in an optical scheme as depicted in FIG. 2; the numerals 1–8 have the same meaning as in FIG. 1, where the primed values denote the path to a second detector. The light passing through optical devices 5, 5', could be sent to separate detectors 7, 7', as shown—or a single detector could be time shared with a light-switching or chopping mechanism well known in the art—with a circuit to form the difference between the signals effected by electronic means 9, 9' to afford the difference signal 10. Alternatively, one could employ a differential detector which will directly do the subtraction. In either case the difference, X-Y, is then seen to be proportional to P, the property of interest.

Another possible embodiment arises through manipulation of (7) and (8). We define Z as:

$$Z = I_{1200} + I_{1625} + I_{1700} + I_{1920}$$

If Z is added to both sides of (8) the result is $$0.25(P-K)+Z = (1+0.25)I_{1200} + (1-0.5)I_{1625} + (1+0.125)I_{1700} + (1-1)I_{1920}$$

In the more general case, starting from (8) affords $$F(P-K)+xZ = (x+b_{1200})I_{1200} + (x+b_{1625})I_{1625} + (x+b_{1700})I_{1700} + (x+b_{1920})I_{1920} \quad (9)$$

where some values of b may be negative and x is a constant which would be selected so that no $(x+b_j)$ would be negative, and the normalization factor F is chosen so that the largest (in absolute magnitude) of $(x+b_j)$ is approximately one, which corresponds to 100% transmission. Rearrangement of (9) then affords (10), $$F(P-K) = (x+b_{1200})I_{1200} + (x+b_{1625})I_{1625} + (x+b_{1700})I_{1700} + (x+b_{1920})I_{1920} - xZ, \text{ or,}$$

$$F(P-K) = A' - xZ. \quad (10)$$

This represents a situation where A' is represented by an optical device with all positive coefficients, and xZ is represented by an optical device with flat and constant transmission at the wavelengths j.

A variety of optical devices can be used in the practice of our invention to effect the optical calculation of a property given by a predictive equation according to (1). In perhaps the simplest embodiment the optical device is a simple filter opaque everywhere but at the wavelengths j corresponding to positive coefficients $b_j$, and whose intensity of light passing through the sample at those wavelengths is proportional to $b_j$. Such an optical feature can be generated by depositing multiple thin films of dielectrics on a transparent substrate. Several—and possibly several tens—of layers could be deposited to generate the entire "shape" of the optical device.

In another embodiment a substrate could be divided into multiple areas, and one area at a time subject to thin film deposition to create each transmission window with intensity of light passing through the sample proportional to $b_j$. Each transmitting area is generated in a unique area of the same substrate, while the other areas are masked off.

A different embodiment has the advantage of being easily manufactured in volume. A substrate is divided into multiple equal areas or elements. A number of areas in random positions are subject to thin film deposition to create multiple areas of a transmission window for one wavelength while all other areas are masked off. T his is repeated for at least as many transmission wavelengths as required for the predictive equation. Note the transmission of each element is maximized and not related to the coefficient. If all the transmissive elements transmit at 100%, then, e.g., for the equation $0.5b_{1200} + 0.25b_{1500} + 1.0b_{1900}$ one would take the substrate and mask off all transmissive elements at wavelengths other than 1200, 1500, and 1900 nm. One then masks off certain areas for the 1200, 1500, and 1900 nm transmissive elements such that the remaining unmasked elements transmitted in the ratio 2:1:4. Of course, areas that did not initially transmit 100% of the radiation could be readily compensated for so that the final ratio 2:1:4 was obtained. Note that large numbers of blanks could be easily manufactured and then appropriate masks made for different ratios of coefficients at different wavelengths.

In yet another embodiment thin films for a single wavelength filter are applied to the end of a single fiber optic with the correct percent transmission for that wavelength's coefficient. Different fibers are fabricated with different wavelengths, each one representing a coefficient. To reduce manufacturing costs multiple fibers of any one coefficient could be manufactured in a single process by temporarily bundling them during processing. To fabricate a multi-coefficient filter, equal numbers of fibers for each coefficient are bundled together randomly to create a "single" multi-coefficient filter. For example, a final filter representing four coefficients could be made by bundling randomly 50 fibers of each coefficient into one fiber strand.

In still another embodiment a bundle of optical fibers is held together while on one end is deposited thin film layers such that the fiber will only pass light of one specific wavelength. In essence a narrow band filter is deposited on the end of multiple fibers. After depositing the "filter" the fibers are separated into individual fiber strands again for each wavelength required. To "assemble" the required function, say that in equation (4), one would bundle randomly 2 fibers with a 1200 nm filter, 4 fibers with a 1625 nm filter, 1 fiber with a 1700 nm filter, and 8 fibers with a 1920 nm filter, or any other combination so long as the ratio at the four wavelengths was 1:2:0.5:4. In this example we assume that each fiber transmits exactly the same amount of light at the relevant wavelength, ideally 100%.

The foregoing methods rely on thin films to manufacture the optical filter, but other methods also could be used. Bragg gratings, i.e., fibers that transmit or reflect a single wavelength, could be used as an alternative in implementation. Optical transmission or reflective devices based on diffractive optics (grooves embedded in a transparent or reflective optical device, similar to a grating) also serve as alternatives. These devices can be fabricated by, e.g., injection molding and etching, as well as by other techniques. Very small diffractive devices also could be fabricated and placed on the ends of optical fibers.

It needs to be emphasized that our invention is independent of the particular kind of optical device used and the electronic circuity in the instrumentation. Many variants are possible, some using even more than 2 detectors, nonetheless it will be clearly seen that all such variants are within the scope of our invention, and each such variant is intended to be subsumed thereunder. The key is the use of an optical device(s) which simultaneously transmits light at multiple wavelengths j in proportion to the coefficients $b_j$ in the predictive equation (3) appropriate for any specified property.

What is claimed is:

1. A method of optical computation of a physical or chemical property, P, of a sample, whose value is given by a predictive equation of the form $$P = K + \sum_{j=1}^{n} b_j I_j$$

where $I_j$ is the intensity of light passing through the sample sample at wavelength j and $b_j$ is the coefficient associated with the intensity passing through the sample of light at wavelength j, n is the number of discrete wavelengths used and is such that $2 \leq n \leq 100$, and K is a constant, comprising passing undispersed electromagnetic radiation of wavelengths from about 150 to about 15,000 nanometers through a sample, conducting radiation transmitted by said sample to an optical device, said optical device being everywhere opaque except at wavelengths j, and where the transmission of light of wavelength j through the optical device is proportional to $b_j$, and simultaneously measuring all of the wavelengths of light transmitted through said optical device.

2. The method of claim 1 where $2 \leq n \leq 50$.

3. A method of optical computation of a physical or chemical property, P, of a sample, whose value is given by a predictive equation of the form $$P = K + \sum_{j=1}^{n} b_j I_j$$

where $I_j$ is the intensity of light passing through the sample at wavelength j and $b_j$ is the coefficient associated with the intensity of light passing through the sample at wavelength j, n is the number of discrete wavelengths used and is such that $2 \leq n \leq 100$, and K is a constant, comprising passing undispersed electromagnetic radiation of wavelengths from about 150 to about 15,000 nanometers through a sample, conducting radiation transmitted by said sample to a pair of optical device, a first optical device being everywhere opaque except at wavelengths j, and where the transmission of light of wavelength j through the optical device is proportional to all positive $b_j$, and a second optical device being everywhere opaque except at wavelengths j, and where the transmission of light of wavelength j through the optical device is proportional to all negative $b_j$, simultaneously measuring all of the wavelengths of light transmitted through each optical device, and forming the difference between the total light passing through said first and second optical device.

4. The method of claim 3 where $2 \leq n \leq 50$.

* * * * *